United States Patent [19]
Brange

[11] Patent Number: 5,597,796
[45] Date of Patent: Jan. 28, 1997

[54] TRANSDERMAL INSULIN

[75] Inventor: Jens J. V. Brange, Klamponborg, Denmark

[73] Assignee: Novo Nordisk A/S, Bagsvaerd, Denmark

[21] Appl. No.: 301,838

[22] Filed: Sep. 7, 1994

Related U.S. Application Data

[63] Continuation of Ser. No. 85,473, Jun. 30, 1993, abandoned, which is a continuation of Ser. No. 751,836, Aug. 30, 1991, abandoned.

[30] Foreign Application Priority Data

Jan. 22, 1991 [DK] Denmark .................. 0101/91

[51] Int. Cl.$^6$ .................. A61K 38/28; A61N 1/30; C07K 14/62
[52] U.S. Cl. .................. 514/3; 424/449; 530/303; 604/20
[58] Field of Search .................. 530/303; 514/3; 204/165, 180.1, 182.6, 183.3, 450, 550; 424/78.02, 449; 604/20, 21

[56] References Cited

U.S. PATENT DOCUMENTS

| | | | |
|---|---|---|---|
| 5,149,777 | 9/1992 | Hansen et al. | 530/303 |
| 5,514,646 | 5/1996 | Chance et al. | 530/303 |

FOREIGN PATENT DOCUMENTS

| | | | |
|---|---|---|---|
| 383472 | 8/1990 | European Pat. Off. | 530/303 |
| 10937 | 11/1989 | WIPO | 530/303 |

OTHER PUBLICATIONS

Library of Congress Data-base from "Internet".
Diabetes Care, vol. 13, No. 9, issued Sep. 1990, Brange et al, "Monomeric Insulins . . . ", pp. 923–954.
Diabetes, vol. 21, issued 1972, Smith, "Amino Acid Sequences of Insulins", pp. 457–460.
Siddiqui et al, "Facilitated Transdermal Transport of Insulin," *J. Pharm. Sci.* 76(4), Apr. 1987. pp. 341–345.
Zimmerman et al, "Guinea Pig Insulin", *J. Biol. Chem.* 249(13), Jul. 10, 1974. pp. 4021–4025.

*Primary Examiner*—Jeffrey E. Russel
*Attorney, Agent, or Firm*—Steve T. Zelson, Esq.; James Harrington, Esq.

[57] ABSTRACT

Insulin analogues have been developed which are well suited for transdermal administration by iontophoresis. The insulin analogues have a negative charge at neutral pH and a reduced tendency to association. They are prepared by altering the human insulin molecule by substituting at least two of the amino acid residues of human insulin by Glu and/or Asp at selected positions in the molecule.

11 Claims, 1 Drawing Sheet

FIG.1

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear     ( i i ) MOLECULE TYPE: protein     ( i x ) FEATURE:
        ( A ) NAME/KEY: Disulfide-bond
        ( B ) LOCATION: 6..11

( i x ) FEATURE:
        ( A ) NAME/KEY: Disulfide-bond
        ( B ) LOCATION: 7
        ( D ) OTHER INFORMATION: /note= "This disulfide bond is
            between residue number 7 of this sequence and
            residue number 7 of SEQ ID NO:2"

( i x ) FEATURE:
        ( A ) NAME/KEY: Disulfide-bond
        ( B ) LOCATION: 20
        ( D ) OTHER INFORMATION: /note= "This disulfide bond is
            between residue number 20 of this sequence and
            residue number 19 of SEQ ID NO:2"

( x i ) SEQUENCE DESCRIPTION: SEQ ID NO:1:

```
Gly  Ile  Val  Glu  Gln  Cys  Cys  Thr  Ser  Ile  Cys  Ser  Leu  Tyr  Gln  Leu
 1                    5                         10                        15

Glu  Asn  Tyr  Cys  Asn
                20
```

( 2 ) INFORMATION FOR SEQ ID NO:2:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear     ( i i ) MOLECULE TYPE: protein     ( i x ) FEATURE:
        ( A ) NAME/KEY: Disulfide-bond
        ( B ) LOCATION: 7
        ( D ) OTHER INFORMATION: /note= "This disulfide bond is
            between residue number 7 of this sequence and
            residue number 7 of SEQ ID NO:1"

( i x ) FEATURE:
        ( A ) NAME/KEY: Disulfide-bond
        ( B ) LOCATION: 19
        ( D ) OTHER INFORMATION: /note= "This disulfide bond is
            between residue number 19 of this sequence and
            residue number 20 of SEQ ID NO:1"

( x i ) SEQUENCE DESCRIPTION: SEQ ID NO:2:

```
Phe  Val  Asn  Gln  His  Leu  Cys  Gly  Ser  His  Leu  Val  Glu  Ala  Leu  Tyr
 1                    5                         10                        15

Leu  Val  Cys  Gly  Glu  Arg  Gly  Phe  Phe  Tyr  Thr  Pro  Lys  Thr
                20                        25                        30
```

( 2 ) INFORMATION FOR SEQ ID NO:3:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear     ( i i ) MOLECULE TYPE: protein ( i x ) FEATURE:
    ( A ) NAME/KEY: Disulfide-bond
    ( B ) LOCATION: 6..11

( i x ) FEATURE:
    ( A ) NAME/KEY: Disulfide-bond
    ( B ) LOCATION: 7
    ( D ) OTHER INFORMATION: /note= "This disulfide bond is between residue number 7 of this sequence and residue number 7 of SEQ ID NO:4"

( i x ) FEATURE:
    ( A ) NAME/KEY: Disulfide-bond
    ( B ) LOCATION: 20
    ( D ) OTHER INFORMATION: /note= "This disulfide bond is between residue number 20 of this sequence and residue number 19 of SEQ ID NO:4"

( i x ) FEATURE:
    ( A ) NAME/KEY: Definition of Xaa
    ( B ) LOCATION: 8
    ( D ) OTHER INFORMATION: /note= "The amino acid in this position is Asp, Glu, Ser, Thr, His or Ile"

( i x ) FEATURE:
    ( A ) NAME/KEY: Definition of Xaa
    ( B ) LOCATION: 9
    ( D ) OTHER INFORMATION: /note= "The amino acid in this position is Asp, Glu, Ser, Thr, His or Ile"

( i x ) FEATURE:
    ( A ) NAME/KEY: Definition of Xaa
    ( B ) LOCATION: 10
    ( D ) OTHER INFORMATION: /note= "The amino acid in this position is Asp, Glu, Ser, Thr, His or Ile"

( i x ) FEATURE:
    ( A ) NAME/KEY: Definition of Xaa
    ( B ) LOCATION: 13
    ( D ) OTHER INFORMATION: /note= "The amino acid in this position is Leu, Asp, Glu, Ser, Thr, His or Ile"

( i x ) FEATURE:
    ( A ) NAME/KEY: Definition of Xaa
    ( B ) LOCATION: 21
    ( D ) OTHER INFORMATION: /note= "The amino acid in this position is Asn, Asp, Glu, Ser, Thr, His or Ile"

( x i ) SEQUENCE DESCRIPTION: SEQ ID NO:3:

Gly Ile Val Glu Gln Cys Cys Xaa Xaa Xaa Cys Ser Xaa Tyr Gln Leu
1               5                   10                  15

Glu Asn Tyr Cys Xaa
            20

( 2 ) INFORMATION FOR SEQ ID NO:4:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear     ( i i ) MOLECULE TYPE: protein     ( i x ) FEATURE:
        ( A ) NAME/KEY: Disulfide-bond
        ( B ) LOCATION: 7
        ( D ) OTHER INFORMATION: /note= "This disulfide bond is between residue number 7 of this sequence and residue number 7 of SEQ ID NO:3"

( i x ) FEATURE:
        ( A ) NAME/KEY: Disulfide-bond
        ( B ) LOCATION: 19
        ( D ) OTHER INFORMATION: /note= "This disulfide bond is between residue number 19 of this sequence and residue number 20 of SEQ ID NO:3"

```
( i x ) FEATURE:
         ( A ) NAME/KEY: Definition of Xaa
         ( B ) LOCATION: 1
         ( D ) OTHER INFORMATION: /note= "The amino acid in this
                 position is Phe, Asp, Glu, Ser, Thr, His or Ile"

( i x ) FEATURE:
         ( A ) NAME/KEY: Definition of Xaa
         ( B ) LOCATION: 2
         ( D ) OTHER INFORMATION: /note= "The amino acid in this
                 position is Val, Asp, Glu, Ser, Thr, His or Ile"

( i x ) FEATURE:
         ( A ) NAME/KEY: Definition of Xaa
         ( B ) LOCATION: 5
         ( D ) OTHER INFORMATION: /note= "The amino acid in this
                 position is Asp, Glu, Ser, Thr, His or Ile"

( i x ) FEATURE:
         ( A ) NAME/KEY: Definition of Xaa
         ( B ) LOCATION: 9
         ( D ) OTHER INFORMATION: /note= "The amino acid in this
                 position is Asp, Glu, Ser, Thr, His or Ile"

( i x ) FEATURE:
         ( A ) NAME/KEY: Definition of Xaa
         ( B ) LOCATION: 10
         ( D ) OTHER INFORMATION: /note= "The amino acid in this
                 position is Asp, Glu, Ser, Thr, His or Ile"

( i x ) FEATURE:
         ( A ) NAME/KEY: Definition of Xaa
         ( B ) LOCATION: 12
         ( D ) OTHER INFORMATION: /note= "The amino acid in this
                 position is Val, Asp, Glu, Ser, Thr, His or Ile"

( i x ) FEATURE:
         ( A ) NAME/KEY: Definition of Xaa
         ( B ) LOCATION: 14
         ( D ) OTHER INFORMATION: /note= "The amino acid in this
                 position is Ala, Asp, Glu, Ser, Thr, His or Ile"

( i x ) FEATURE:
         ( A ) NAME/KEY: Definition of Xaa
         ( B ) LOCATION: 16
         ( D ) OTHER INFORMATION: /note= "The amino acid in this
                 position is Tyr, Asp, Glu, Ser, Thr, His or Ile"

( i x ) FEATURE:
         ( A ) NAME/KEY: Definition of Xaa
         ( B ) LOCATION: 17
         ( D ) OTHER INFORMATION: /note= "The amino acid in this
                 position is Leu, Asp, Glu, Ser, Thr, His or Ile"

( i x ) FEATURE:
         ( A ) NAME/KEY: Definition of Xaa
         ( B ) LOCATION: 18
         ( D ) OTHER INFORMATION: /note= "The amino acid in this
                 position is Val, Asp, Glu, Ser, Thr, His or Ile"

( i x ) FEATURE:
         ( A ) NAME/KEY: Definition of Xaa
         ( B ) LOCATION: 20
         ( D ) OTHER INFORMATION: /note= "The amino acid in this
                 position is Gly, Asp, Glu, Ser, Thr, His or Ile"

( i x ) FEATURE:
         ( A ) NAME/KEY: Definition of Xaa
         ( B ) LOCATION: 26
         ( D ) OTHER INFORMATION: /note= "The amino acid in this
                 position is Tyr, Asp, Glu, Ser, Thr, His or Ile"

( i x ) FEATURE:
         ( A ) NAME/KEY: Definition of Xaa
         ( B ) LOCATION: 27
         ( D ) OTHER INFORMATION: /note= "The amino acid in this
                 position is Asp, Glu, Ser, Thr, His or Ile"

( i x ) FEATURE:
```

(A) NAME/KEY: Definition of Xaa
(B) LOCATION: 28
(D) OTHER INFORMATION: /note= "The amino acid in this
position is Pro, Asp, Glu, Ser, Thr, His or Ile"

( x i ) SEQUENCE DESCRIPTION: SEQ ID NO:4:

```
Xaa Xaa Asn Gln Xaa Leu Cys Gly Xaa Xaa Leu Xaa Glu Xaa Leu Xaa
1               5                   10                      15
Xaa Xaa Cys Xaa Glu Arg Gly Phe Phe Xaa Xaa Xaa Lys Thr
            20                  25                  30
```

( 2 ) INFORMATION FOR SEQ ID NO:5:

( i ) SEQUENCE CHARACTERISTICS:
(A) LENGTH: 21 amino acids
(B) TYPE: amino acid
(C) STRANDEDNESS: single
(D) TOPOLOGY: linear ( i i ) MOLECULE TYPE: protein ( i x ) FEATURE:
(A) NAME/KEY: Disulfide-bond
(B) LOCATION: 6..11

( i x ) FEATURE:
(A) NAME/KEY: Disulfide-bond
(B) LOCATION: 7
(D) OTHER INFORMATION: /note= "This disulfide bond is
between residue number 7 of this sequence and
residue number 7 of SEQ ID NO:6"

( i x ) FEATURE:
(A) NAME/KEY: Disulfide-bond
(B) LOCATION: 20
(D) OTHER INFORMATION: /note= "This disulfide bond is
between residue number 20 of this sequence and
residue number 19 of SEQ ID NO:6"

( i x ) FEATURE:
(A) NAME/KEY: Definition of Xaa
(B) LOCATION: 5
(D) OTHER INFORMATION: /note= "The amino acid in this
position is Gln, Asp or Glu"

( i x ) FEATURE:
(A) NAME/KEY: Definition of Xaa
(B) LOCATION: 12
(D) OTHER INFORMATION: /note= "The amino acid in this
position is Ser, Asp or Glu"

( i x ) FEATURE:
(A) NAME/KEY: Definition of Xaa
(B) LOCATION: 14
(D) OTHER INFORMATION: /note= "The amino acid in this
position is Tyr, Asp or Glu"

( i x ) FEATURE:
(A) NAME/KEY: Definition of Xaa
(B) LOCATION: 15
(D) OTHER INFORMATION: /note= "The amino acid in this
position is Gln, Asp or Glu"

( i x ) FEATURE:
(A) NAME/KEY: Definition of Xaa
(B) LOCATION: 18
(D) OTHER INFORMATION: /note= "The amino acid in this
position is Asn, Asp or Glu"

( i x ) FEATURE:
(A) NAME/KEY: Definition of Xaa
(B) LOCATION: 21
(D) OTHER INFORMATION: /note= "The amino acid in this
position is Asn, Asp or Glu"

( x i ) SEQUENCE DESCRIPTION: SEQ ID NO:5:

```
Gly  Ile  Val  Glu  Xaa  Cys  Cys  Thr  Ser  Ile  Cys  Xaa  Leu  Xaa  Xaa  Leu
1                   5                        10                  15

Glu  Xaa  Tyr  Cys  Xaa
               20
```

( 2 ) INFORMATION FOR SEQ ID NO:6:

( i ) SEQUENCE CHARACTERISTICS:
        ( A ) LENGTH: 32 amino acids
        ( B ) TYPE: amino acid
        ( C ) STRANDEDNESS: single
        ( D ) TOPOLOGY: linear     ( i i ) MOLECULE TYPE: protein     ( i x ) FEATURE:
        ( A ) NAME/KEY: Disulfide-bond
        ( B ) LOCATION: 7
        ( D ) OTHER INFORMATION: /note= "This disulfide bond is
            between residue number 7 of this sequence and
            residue number 7 of SEQ ID NO:5"

( i x ) FEATURE:
        ( A ) NAME/KEY: Disulfide-bond
        ( B ) LOCATION: 19
        ( D ) OTHER INFORMATION: /note= "This disulfide bond is
            between residue number 19 of this sequence and
            residue number 20 of SEQ ID NO:5"

( i x ) FEATURE:
        ( A ) NAME/KEY: Definition of Xaa
        ( B ) LOCATION: 1
        ( D ) OTHER INFORMATION: /note= "The amino acid in this
            position is Phe, Asp or Glu"

( i x ) FEATURE:
        ( A ) NAME/KEY: Definition of Xaa
        ( B ) LOCATION: 2
        ( D ) OTHER INFORMATION: /note= "The amino acid in this
            position is Val, Asp or Glu"

( i x ) FEATURE:
        ( A ) NAME/KEY: Definition of Xaa
        ( B ) LOCATION: 3
        ( D ) OTHER INFORMATION: /note= "The amino acid in this
            position is Asn, Asp or Glu"

( i x ) FEATURE:
        ( A ) NAME/KEY: Definition of Xaa
        ( B ) LOCATION: 4
        ( D ) OTHER INFORMATION: /note= "The amino acid in this
            position is Gln, Asp or Glu"

( i x ) FEATURE:
        ( A ) NAME/KEY: Definition of Xaa
        ( B ) LOCATION: 9
        ( D ) OTHER INFORMATION: /note= "The amino acid in this
            position is Ser, Asp or Glu"

( i x ) FEATURE:
        ( A ) NAME/KEY: Definition of Xaa
        ( B ) LOCATION: 10
        ( D ) OTHER INFORMATION: /note= "The amino acid in this
            position is His, Asp or Glu"

( i x ) FEATURE:
        ( A ) NAME/KEY: Definition of Xaa
        ( B ) LOCATION: 16
        ( D ) OTHER INFORMATION: /note= "The amino acid in this
            position is Tyr, Asp or Glu"

( i x ) FEATURE:
        ( A ) NAME/KEY: Definition of Xaa
        ( B ) LOCATION: 18
        ( D ) OTHER INFORMATION: /note= "The amino acid in this
            position is Val, Asp or Glu"

( i x ) FEATURE:

(A) NAME/KEY: Definition of Xaa
(B) LOCATION: 20
(D) OTHER INFORMATION: /note= "The amino acid in this position is Gly, Asp or Glu"

(ix) FEATURE:
(A) NAME/KEY: Definition of Xaa
(B) LOCATION: 22
(D) OTHER INFORMATION: /note= "The amino acid in this position is Arg, Asp or Glu"

(ix) FEATURE:
(A) NAME/KEY: Definition of Xaa
(B) LOCATION: 26
(D) OTHER INFORMATION: /note= "The amino acid in this position is Tyr, Asp or Glu"

(ix) FEATURE:
(A) NAME/KEY: Definition of Xaa
(B) LOCATION: 27
(D) OTHER INFORMATION: /note= "The amino acid in this position is Thr, Asp or Glu"

(ix) FEATURE:
(A) NAME/KEY: Definition of Xaa
(B) LOCATION: 28
(D) OTHER INFORMATION: /note= "The amino acid in this position is Pro, Asp or Glu"

(ix) FEATURE:
(A) NAME/KEY: Definition of Xaa
(B) LOCATION: 29
(D) OTHER INFORMATION: /note= "The amino acid in this position is Lys, Asp or Glu"

(ix) FEATURE:
(A) NAME/KEY: Definition of Xaa
(B) LOCATION: 30
(D) OTHER INFORMATION: /note= "The amino acid in this position is Thr, Asp or Glu"

(ix) FEATURE:
(A) NAME/KEY: Definition of Xaa
(B) LOCATION: 31
(D) OTHER INFORMATION: /note= "The amino acid in this position is Asp or Glu or is absent"

(ix) FEATURE:
(A) NAME/KEY: Definition of Xaa
(B) LOCATION: 32
(D) OTHER INFORMATION: /note= "The amino acid in this position is Asp or Glu or is absent"

(xi) SEQUENCE DESCRIPTION: SEQ ID NO:6:

Xaa Xaa Xaa Xaa His Leu Cys Gly Xaa Xaa Leu Val Glu Ala Leu Xaa
1               5                   10                      15

Leu Xaa Cys Xaa Glu Xaa Gly Phe Phe Xaa Xaa Xaa Xaa Xaa Xaa Xaa
        20              25                      30

TRANSDERMAL INSULIN

This application is a continuation of application Ser. No. 08/085,473, filed Jun. 30, 1993, now abandoned, which is a continuation of application Ser. No. 07/751,836, filed Aug. 30, 1991, now abandoned, the contents of which are incorporated herein by reference.

FIELD OF INVENTION

The present invention relates also to novel insulin analogues that are well adapted to transdermal administration by iontophoresis, to pharmaceutical composition containing the novel insulin analogues, and to the transdermal administration of monomeric insulin analogues by iontophoresis.

BACKGROUND OF THE INVENTION

The transdermal administration of drugs in order to obtain systemic effects has gained increasing recognition in recent years as being a feasible mode for parenteral administration. More and more transdermal administration is being used for delivery of low molecular weight drugs, i.e., small size, drugs. The usual mode of transdermal delivery is through passive diffusional transport of the drug across the skin barrier. The scopolamine patch, the oestradiol patch and the nitroglycerin patch to which this mode of administration has been applied all contain low molecular weight drugs which are lipophilic (hydrophobic) in character.

However, passive transdermal delivery is not well suited to, and may not even be possible for drugs which are low in skin permeability. Unfortunately, such drugs include pharmacologically active hydrophilic peptide compounds, notably insulin.

In order to obviate the limitations on passive forms of transdermal delivery, the art has considered iontophoresis for systemic delivery of ionizing hydrophilic drugs. Iontophoresis may be described as being the transfer of solutes through a biologic membrane under the influence of an electrical field. Iontophoresis has been considered for administering insulin.

Transport through the skin by iontophoresis is believed to occur primarily through aqueous filled pores in the skin, e.g., sweat ducts. Since the net polarity of the pores in human skin is negative at neutral pH, delivery of positively charged molecules therethrough can be facilitated by application of an electrical current. However, the mean size of these pores is believed to be in the order of about 20 Angstrom, and, therefore the iontophoretic flow of a pharmacologically active compound through the skin in amounts adequate for the medical needs to be served by such compound is most feasible if the molecule of the compound is about 20 Å in diameter or smaller.

The efforts made by the art, heretofore, to administer insulin through iontophoresis have been without great success. See Stephen et al. "Potential novel methods for insulin administration: I. Iontophoresis", Biomed. Biochim. Acta 43 (1984) 5, 553–558. Stephen et al. attributed their failure to force insulin across the skin barrier in pharmacologically adequate amounts to the relatively large size of the hexamer form of the insulin molecules (in solution). Stephen et al. postulated that a more strongly ionized predominantly monomeric form of insulin might successfully be administered transdermally by iontophoresis.

Subsequent to the work of Stephen et al. other investigators have reported achieving a more successful transdermal transport of human insulin by iontophoresis, see Meyer et al., "Transdermal Delivery of Human Insulin to Albino Rabbits Using Electrical Current", The American Journal of Medical Sciences, May 1989, Vol. 297, No. 5, pp. 321–325 and Ovais Siddiqui et al., "Facilitated Transdermal of Insulin", Journal of Pharmaceutical sciences, vol. 76, No. 4, Apr. 1987, pp. 341–345.

In the treatment of diabetes, injection or infusion of a predetermined quantity of insulin is presently required in order to maintain a therapeutically effective level of insulin in the blood. Due to the discomfort of the several daily injections of insulin that typically are administered, much effort has been expanded by the art over the years to find an administration route for insulin, other than through injection. Transdermal iontophoretic delivery offers the potential for being a superior route for administration of insulin. However, molecules of the usual insulin compound administered, e.g., the porcine insulin or human insulin, that heretofore has been conventional in the pharmaceutical compositions, is present in solution in such compositions in an associated form, notably as dimers and hexamers, the latter being the predominant association species.

The insulin hexamer has the shape of a slightly flattened sphere. The diameter of the insulin hexamer is approximately 50 Å, which diameter is believed to be too large for transdermal delivery (through the pores in the skin) in sufficient quantities to generate the therapeutically needed blood levels of insulin.

However, monomeric insulin analogues would have a smaller diameter and adequate dosage levels of such insulin compounds might be driven across the skin barrier through iontophoresis in therapeutically effective amounts.

STATEMENT OF THE INVENTION

Briefly stated, the method of this invention comprises transdermally administering at least 5 IU (International Units) per day of a predominantly monomer form insulin analogue from an aqueous medium, e.g. a solution or a gel, containing it. The method comprises placing an aqueous medium of the monomeric insulin analogue in contact with human skin then applying direct current to said insulin analogue medium and therethrough to the skin in contact with the medium. Pharmacologically effective quantities of the insulin analogue then cross the skin barrier through iontophoresis. The monomeric insulin analogue employed in practice of this invention is characterized by exhibiting a greater negative charge of at least one unit at neutral pH than that exhibited by human insulin.

By "insulin analogue" as used herein is meant a compound with insulin acitvity having a molecular structure similar to that of a naturally occurring insulin including the disulphide bridges between A(7)Cys and B(7)Cys, between A(20)Cys and B(19)Cys and between A(6)Cys and A(11)Cys, and which compound has been modified by exchange, deletion or addition of at least one amino acid residue.

Desirably, the insulin analogue medium is made the cathode in the electrical circuit through the skin and the pH of the insulin analogue medium is in the range of pH 4–8.

One mode of preferred practice of the method of the invention employs monomeric insulin analogues described in copending application Ser. No. 901,821, filed Aug. 29, 1986, the disclosure of which is incorporated herein by this reference thereto. Referenced also are the publications which relate to that invention, namely, J. Brange et al., "Monomeric insulin obtained by protein engineering and their medical implications", Nature, Vol. 333, No. 6174, pp. 679–682, Jun. 16, 1988; and Jens Brange et al., "Monomeric Insulins and Their Experimental and Clinical Implications", Diabetes Care, Vol. 13, No. 9, Sept. 1990.

Another mode of this invention comprises certain novel insulin analogues particularly adapted for transdermal delivery through iontophoresic transport. Generally, these insulin analogues correspond to the formula III provided hereinafter.

BRIEF DESCRIPTION OF THE FIGURE

For further understanding of this method reference is now made to the attached drawing whereon is shown a schematic illustration of the apparatus usable in practice of the present invention.

Figure 1:
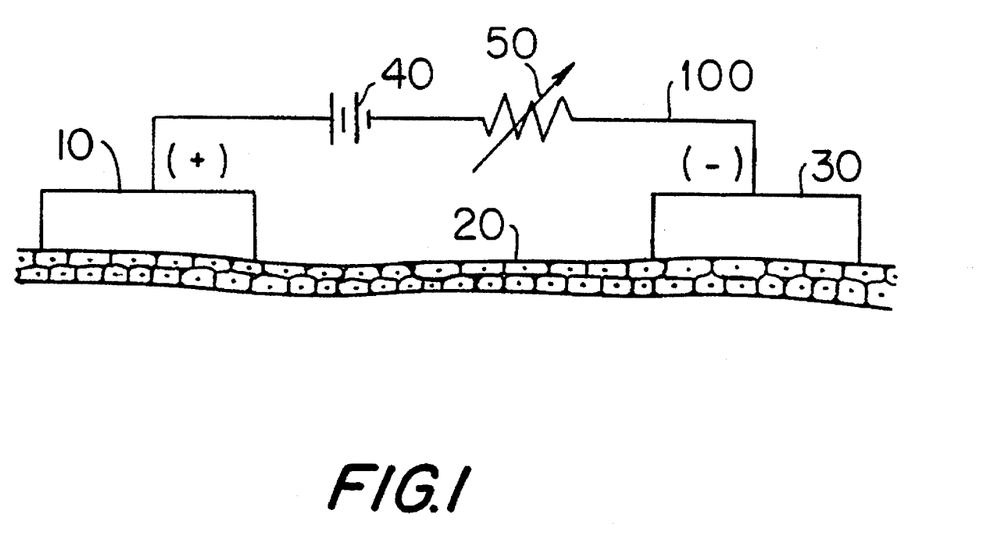

It may be seen that an electrically conductive pad 10, which desirably is a reservoir of normal saline (0.9% by wt) preferably at pH 6–8 is made the anode of an electrical circuit 100 which includes the skin 20, a cathode 30, which cathode comprises an electrically conductive solution or gel that contains a monomeric insulin analogue in concentrations of 10 IU/ml to 10.000 IU/ml.

Also present in circuit 100 is a power source illustrated herein as battery 40 and a variable resistor 50 whose purpose is to control the current density applied to the skin.

In the preferred mode of invention herein illustrated, the pH of the insulin medium in cathode 30 is in the preferred range of pH 4–8. If, however, pH of the insulin medium is adjusted to less than the isoelectric point of the insulin analogue, which in practice of this invention is at about pH 5 or less, the insulin medium may be made the anode of the circuit, and such also is contemplated in practice of this invention. Desirably, the concentration of the insulin analogue in the insulin medium is in the range of 100–1000 IU/ml and cathode 30 may be a solution soaked pad containing 1–5 ml of such insulin solution. Anode 10 may also be a solution soaked pad.

The current density applied to the skin is maintained relatively low, desirably being less than about 1 milliampere per square centimeter of the skin area in contact with the insulin solution. To increase the dosage level, the area of the cathode pad or patch 30 containing the insulin solution may be increases so as to cover skin area in whatever proportions are desired. In practice of the invention, a variable resistor and a battery are adequate for attaining current density levels of less than 1 mA/cm$^2$ for solution soaked pads of 5 or 10 cm$^2$. For example, the insulin solution soaked pad cathode may be 5 cm$^2$ and the saline soaked pad may be 10 cm$^2$ in area and the applied current at the cathode 0.4 mA. A suitable current density range for administering a therapeutically effective dose of insulin is 0.1–1.0 mA/cm$^2$.

The current flow for the iontophoresis transdermal administration may be continuous or pulsating. The preferred administration time will vary according to the dose level sought and may, of course, also be somewhat different for each individual.

By and large the rate of permeation of the insulin analogue through the skin under iontophoresis will depend upon the particular insulin analogue being administered, the insulin concentration in the solution, the ion strength of the solution which depends i.a. on presence of ions such as Na$^+$ and Cl$^-$, the current density, area of skin covered by the solution, and of course the duration of the iontophoresis.

DISCUSSION OF THE MONOMERIC INSULIN ANALOGUES

It is well known that the molecules of human or porcine insulin in the relatively concentrated solution normally employed for sub-cutaneous administration (of say U-40 or U-100 strength, the latter corresponding generally to 0.6 mM), are largely perhaps entirely in an associated form, being predominantly in hexamers, usually as hexameric Zn-insulin. And the hexamer is too big for effective transdermal administration even through iontophoresis. Studies have shown that a 50 to 100 fold dilution of these U-40 or U-100 insulin solutions is required to disassociate the hexamers into dimers. A substantial further dilution (of perhaps a 1000 fold) is necessary before the dominant form of the human or porcine insulin molecules in the aqueous solution as the monomer. The normal concentration of human insulin in blood is about $10^{-9}$ to $10^{-10}$ M and at this concentration level the insulin molecules are not associated. That is to say, the insulin molecules in blood are monomeric. The well known lag in insulin activity which occurs post sub-cutaneous administration of insulin solutions, has been attributed to the time lag before the hexamers and dimers disassociate into the monomeric active form. Thus, human insulin analogues which remain in monomer form in the relatively concentrated insulin mediums contemplated for practice of this invention are in themselves advantageous for being rapid acting.

The above-mentioned Brange et al. papers discuss monomeric insulins and the clinical implications of monomeric insulins. The monomeric insulin analogues described by Brange et al. in their papers and in Ser. No. 901,821, filed Aug. 29, 1986, are pointed out to be advantageous because they do not exhibit the delayed onset of insulin activity which characteristically takes place upon administration of human or porcine insulin in solution at the same concentration.

As has already been recognized by the art the hexamer form of human and porcine insulin is disadvantageous for iontophoresis induced transdermal administration because of the large size of the insulin hexamer. On the other hand, monomeric insulin would be advantageous for transdermal administration for being a small enough molecule to cross the skin barrier via the pores of the skin. Thus, although transdermally administering human or porcine insulin in monomer form solution is impractical for requiring an excessively dilute insulin solution such is not so for the insulin analogues described in the Brange et al. papers supra, and in copending Ser. No. 901,821, filed Aug. 29, 1986.

Accordingly, the preferred insulin analogues disclosed by Brange et al. in copending Ser. No. 901,821, filed Aug. 29, 1986, and insulin analogues corresponding to the formula II provided hereinafter are highly advantageous insulin analogues in practice of this invention and are preferred in practice of this invention. The rapid action aspect of these monomer form insulin analogues is a separate advantage. However, it must be appreciated that the invention of Ser. No. 901,821 and the present invention are separate and distinct inventions. They do not coincide. In specific, they overlap with regard to the sort of insulin analogues that comprise preferred embodiments. Some preferred embodiment insulin analogues of this invention are more negatively charged insulin analogues than are preferred embodiments of Ser. No. 901,821.

Thus, practice of this invention contemplates employment of a human insulin analogue wherein amino acid residue substitution(s) have been made so that the human insulin analogue is both monomeric and is more negatively charged at neutral pH than human insulin.

For exemplary practice of this invention reference is made to Stephen et al. supra, to Meyer et al supra and to Siddigui et al. supra. The experimental arrangements and conditions described by each of these papers constitute preferred mode practice of this invention as of the date hereof using, however, a human insulin analogue as described herein, e.g., iontophoresis induced transdermal administration from a 100 IU/ml aqueous solution of the B9 Glu, A12 Glu herein exemplified.

Below reproduced as formula I is a representation of the human insulin molecule whereon are added the letters F to indicate the amino acid residues involved in the association of two insulin molecules into dimer form. Indicated in formula I by the letters E are the amino acid residues involved in the association of 3 insulin dimers into the $Zn^{2+}$ insulin hexamer (B(20) Gly is involved with both the dimer and the hexamer).

bulky amino acid residue or be a more acidic amino acid residue, particularly preferred being Glu and Asp. Fortuitously, many of the E and F residues are at positions in the insulin molecule that are not essential for insulin activity. Therefore, the substitutions made so as to reduce association of the molecules and thereby retain monomeric form for the insulin analogue in solution, do not destroy insulin activity. At numerous other locations in the human insulin molecule substitutions also may be made without destroying insulin activity.

Below reproduced is formula II whereon the letter X indicates the positions wherein substitutions of amino acid residues are contemplated by the invention of the aforementioned Brange et al. patent application Ser. No. 901,821, filed Aug. 29, 1986, so as to generate rapid acting, i.e., monomeric, insulin analogues. To repeat, the preferred insulin analogues according to Ser. No. 901,821 are preferred insulin analogues for practice of this invention as well.

(I)

As already has been pointed out, insulin analogues exhibiting a reduced tendency to self-associate into dimers and hexamers may be generated by substituting one or more of the E and F residues with other naturally occurring amino acid residues through recombinant DNA techniques. The substitute residues should be more hydrophilic than the naturally occurring amino acid residue replaced or be a more B-Chain (contd.)

Phe—X—X—X—Lys—Thr    (SEQ ID NO: 4)
25   26  27  28   29    30

Thus, the amino acid residues substitutions are preferably chosen from among the group consisting of Asp, Glu, Ser, Thr, His, and Ile and are more preferably negatively charged amino acid residues, i.e., Asp and/or Glu.

The novel insulin analogues may preferably contain Asp and/or Glu instead of one or more of the hydroxy amino acids of human insulin, or instead of one or more Gln and Asn of human insulin.

The novel insulin analogues may furthermore preferably contain Ser and/or Thr or Asp and/or Glu instead of one or more of the amino acid residues of human insulin with an aliphatic and/or aromatic side chain.

Preferred sites of substitutions are at the sites B9, B10, B16, B26, B27, and B28, preferably B9, B16, B26, and B28, in which positions one substitution can be sufficient for obtaining a reduced tendency to self-association.

The amino acid residue substitution in position B9 may be chosen from the group consisting of Asp, Pro, Glu, Ile, Leu, Val, His, Thr, Gln, Asn, Met, Tyr, Trp and Phe and more preferably from the group consisting of Asp, Glu, Gln, Asn, and His.

A particular aspect to practice of this invention of importance is that the monomeric insulin analogue should exhibit a greater negative charge at neutral pH than that of human insulin. The difference should be at least 1 negative charge and the isoelectric point of the insulin analogue should be 5 or less.

It is noted that substituting an acidic amino acid residue such as Glu or Asp for a neutral amino acid residue such as the Asn at A21 or for the Ser at B9 involves a shift of 1 negative charge for each such change. Changing a basic amino acid residue such as the Lys at B29 into Glu or Asp involves a 2 negative charge shift.

A pattern of amino acid residue substitutions falling within preferred practice of this invention is set out by formula III below. Some of the insulin analogues in formula III are novel. Characteristically, the insulin analogues of this invention according to formula III contain multiple substitutions, 3–7 substitutions being preferred in practice of this invention.

The amino acid residue substitution in position B10 may be chosen from the group consisting of Asp, Arg, Glu, Asn, and Gln.

In positions B26, B27, and B28 the amino acid residue substitutions are preferably Asp or Glu.

In the remaining positions of the insulin molecule at least two substitutions (preferably in combination with the above mentioned positions) seem to be necessary to obtain the improved properties.

Practice of this invention involves certain preferences of its own. For example, the preference for Glu and Asp as the substitute amino acid residue is stronger. Desirably, the acidic amino acid residues make the insulin molecule more negative.

The above formula III sets out the different positions at which substitute amino acid residues are in the preferred insulin analogues of this invention. The positions indicated as X, Y, Z and W in the human insulin molecule are the locations contemplated for the substitutions. Extensive studies on substitutions generated through chemical synthesis or recombinant DNA techniques and by analysis of naturally occurring insulins have established that amino acid residue substitution at the X, Y, Z and W positions by other amino acid residues which can be coded for by the genetic code is possible without destroying the insulin activity of the resulting insulin analogue.

The X positions are preferred locations in the insulin molecule for making amino acid residue substitutions so as to prevent association of the insulin molecule (in solution) into dimers and thereby to generate solutions of a monomeric insulin analogue. The Z positions are further locations involved in aggregation of the human insulin molecule. The Y and W positions are locations which for one reason or another are particularly good positions for introducing a substitute amino acid residue carrying a negative charge at neutral pH (Asp or Glu).

In formula III the amino acid residue in at least one of the positions designated X or Z and furthermore the amino acid residue in at least one of the positions designated Y or W independently is substituted by Asp or Glu while any remaining X, Y, Z or W designated the amino acid residue occuring in human insulin in the pertinent position, the terminal ends of the B-chain optionally being extended by one or two amino acid residues which can be chosen independently among Asp and Glu.

One group of the above insulin analogues are such wherein in formula III one amino acid residue in a position designated X and furthermore the amino acid residue in at least one of the positions designated Y, Z or W independently is substituted by Asp or Glu while any remaining X, Y, Z or W designates the amino acid residue occuring in human insulin in the pertinent position, the terminal ends of the B-chain optionally being extended by one or two amino acid residues which can be chosen independently among Asp and Glu.

Another preferred group are such wherein in formula III two amino acid residues in positions designated X or Z and furthermore the amino acid residue in at least one of the positions designated Y or W independently is substituted by Asp or Glu while any remaining X, Y, Z or W designates the amino acid residue occuring in human insulin in the pertinent position, the terminal ends of the B-chain optionally being extended by one or two amino acid residues which can be chosen independently among Asp and Glu.

In the above insulin analogues one, two or three amino acid residues in a position designated W may independently be substituted with Asp or Glu. Also one, two or three of the amino acid residues in a position designated Y may independently be substituted by Asp or Glu.

If no W is substituted in formula III, or if the terminal ends of the B-chain have not been extended, then the total number of substitutions is preferably at least five. Preferred X positions for substitution are B9, B16, B26 and B28.

Examples of insulin analogues according to the present invention are GluB9, GluA12 human insulin, AspB9, GluA12 human insulin, GluB9,AspA12 human insulin, GluB9,GluA14 human insulin, GluB9,GluB22,GluB26 human insulin, AspB9,GluB22,GluB26,AspA21 human insulin, GluB16,GluB3,AspA12,AspA21 human insulin, GluB16,GluB22 human insulin, AspB16,GluB22 human insulin GluB16,AspA14 human insulin, GluB16,AspA14, GluB21 human insulin, GluB26,GluB29 human insulin, AspB26,GluB30 human insulin, AspB28,GluA12 human insulin, AspB2,GluB16,AspA12,AspA21 human insulin, GluB29,GluB3,GluB9 human insulin, GluB9,AspB22, B31Glu human insulin, AspB9,AspB16,GluB26,GluB28, AspA21 human insulin, AspB16,AspB26,GluB31,AspB32 human insulin, AspB22,GluB26 human insulin, GluB9, AspB22,GluB31 human insulin and AspB1,AspB4,AspB10, AspB16,GluB27 human insulin.

The novel insulin analogues according to the present invention may be prepared by altering the proinsulin gene through replacement of codon(s) at the appropriate site in the native human proinsulin gene by codon(s) encoding the desired amino acid residue substitute(s) or by synthesizing the whole DNA-sequence encoding the desired insulin analogue. The gene encoding the desired insulin analogue is then inserted into a suitable expression vector which when transferred to a suitable host organism, e.g. E. coli, Bacillus or yeast, generates the desired product. The expressed product is then isolated from the cells or the culture broth depending on whether the expressed product is secreted from the cells or not.

The novel insulin analogues may also be prepared by chemical synthesis by methods analogueue to the method described by Márki et al. (Hoppe-Seyler's Z. Physiol. Chem., 360 (1979), 1916–1632). They may also be formed from separately in vitro prepared A- and B-chains containing the appropriate amino acid residue substitutions, whereupon the modified A- and B-chains are linked together by establishing disulphide bridges according to known methods (e.g. Chance et al., In: Rick DH, Gross E (eds) Peptides: Synthesis - Structure - Function. Proceedings of the seventh American peptide symposium, Illinois, pp. 721–728).

The insulin analogues may furthermore be prepared by a method analogous to the method described in EP patent application No. 0163529A, the disclosure of which is incorporated by reference hereinto. By such a method an insulin precursor of human insulin wherein $Lys^{B29}$ is connected to $Gly^{A21}$ by means of either a peptide bond or a peptide chain or varying length with correctly positioned disulphide bridges is expressed and secreted by yeast and then converted into human insulin by the so-called transpeptidation reaction.

Accordingly the present insulin analogues may be prepared by inserting a DNA-sequence encoding a precursor of the insulin analogue in question into a suitable yeast expression vehicle which then transferred to yeast is capable of expressing and secreting the precursor of the insulin analogue in which $Lys^{B29}$ is connected to $Gly^{A21}$ by a peptide bond or a peptide chain with the formula IV:

$$—R_n—R^1—\qquad\text{(IV)}$$

wherein R is a peptide chain with n amino acid residues, n is an integer from 0 to 33 and $R^1$ is Lys or Arg when culturing the transformed yeast strain in a suitable nutrient medium. The precursor is then recovered from the culture broth and reacted with an amino compound of the formula V:

$$R^2—R^3—R^4—OR^5\qquad\text{(V)}$$

wherein $R^2$ it Thr, Asp or Glu, $R^3$ and $R^4$ are each either Glu or Asp or a peptide bond, and $R^5$ is a carboxy protecting group (e.g. methyl or tert-butyl), using trypsin or trypsin-like enzyme as a catalyst in a mixture of water and organic solvent analogously as described in U.S. Pat. No. 4,343,898 (the disclosure of which is incorporated by reference hereinto) whereupon the carboxy protecting group is removed and the insulin analogue is isolated from the reaction mixture.

The insulin analogues may also be prepared by a method analogue to the method described in EP patent application No. 86302133.3 the disclosure of which is incorporated by reference hereinto. By this method insulin precursors of the type having a bridge between the A- and B-chain consisting of a single pair of basic amino acid (Lys, Arg) are made in yeast and then converted into insulin by an enzymatic conversion.

PREPARATION OF THE NOVEL INSULIN ANALOGUES

Genes encoding the precursors of the insulin analogue can be prepared by modification of genes encoding the corresponding human insulin precursors by site specific mutagenesis to insert or substitute with codons encoding the desired mutations. A DNA-sequence encoding the precursor of the insulin analogue may also be made by enzymatic synthesis form oligonucleotides corresponding in whole or part to the insulin analogue precursor gene.

DNA-sequence containing a gene with the desired mutation are then combined with a suitable promoter sequence, e.g. fragments coding for the TPI promoter ($TPI_P$) (T. Alber and G. Kawasaki., Nucleotide Sequence of the triose Phosphate Isomerase Gene of *Saccharomyces cerevisiae*. J. Mol. Applied Genet. 1 (1982), 419–434), a suitable leader sequence and possible transcription termination sequence, e.g. from TPI of *S. cerevisiae* ($TPI_T$). These fragments provide sequences to ensure a high rate of transcription for the precursor encoding gene and also provide a presequence which can effect the localization of precursor into the secretory pathway and its eventual excretion into the growth medium. The expression units are furthermore provided with a yeast origin of replication, for instance the 2μ origin, and a selectable marker, for instance LEU 2.

For the purpose of this invention we prepared the genes encoding the insulin analogue precursor in question by ligation of oligonucleotides followed by insertion of the gene into a yeast expression plasmid as described by L. Thim et al., Proc. Natl. Acad. Sci. USA 83 (1986), 6766–6770, and J. Markussen et al., Protein Engineering 1 (1987), 215–223.

EXAMPLE 1

Production of B9Glu,A12Glu Human Insulin

A synthetic gene for the precursor B9Glu,B(1–29)-Ala-Ala-Lys-A21Glu,A(1–21) was constructed from oligonucleotides by ligation. The oligonucleotides were synthesized on an automatic DNA synthesizer using phosphoramidite chemistry on a controlled pore glass support (Beaucage, S. L. and Caruthers, M. H. Tetrahydron Letters 22 (1981), 1859–1869). The synthetic gene was obtained as follows:

By a method analogous to that described in WO89/10937 a plasmid encoding the following sequence $TPI_P$-MFα1-signal-leader(1–85)-precursor gene-$TPI_T$ where MFα1 is the *S. cerevisiae* MFα1 coding sequence (Kurjan, J. and Herskowitz, I., Cell 30 (1982), 933–943) and signal-leader(1–85) means that the sequence contains the first 85 amino acid residues of the MFα1 signal-leader sequence was obtained.

An *S. cerevisiae* (E2-7B XE11-36 a/α, Δtpi Δtpi, pep 4-3/pep 4-3) was grown on YPGaL (1% Bacto yeast extract, 2% Bacto peptone, 2% galactose, 1% lactate) to an O.D. at 600 nm of 0.6.

100 ml of culture was harvested by centrifugation, washed with 10 ml of water, recentrifuged and resuspended in 10 ml of a solution containing 1.2 M sorbitol, 25 mM $Na_2EDTA$ pH=8.0, and 6.7 mg/ml dithiothreitol. The suspension was incubated at 30° C. for 15 minutes, centrifuged and the cells resuspended in 10 ml of a solution containing 1.2 M sorbitol, 10 mM $Na_2EDTA$, 0.1 M sodium citrate, pH=5.8, and 2 mg Novozym$^{(R)}$ 234. The suspension was incubated at 30° C. for 30 minutes, the cells collected by centrifugation, washed in 10 ml of 1.2 M sorbitol and 10 ml of CAS (1.2 M sorbitol, 10 mM $CaCl_2$, 10 mM Tris-HCl (Tris=Tris(hydroxymethyl)aminomethane) pH=7.5) and resuspended in 2 ml of CAS. For transformation 0.1 ml of CAS-resuspended cells were mixed with approximately 1 μg of the above described plasmid and left at room temperature for 15 minutes. 1 ml of (20% polyethyleneglycol 4000, 10 mM $CaCl_2$, 10 mM Tris-HCl, pH=7.5) was added and the mixture was centrifuged and the pellet resuspended in 0.1 ml of SOS (1.2 M sorbitol, 33% v/v YPD, 6.7 mM $CaCl_2$, 14 μg/ml leucine) and incubated 30° C. for 2 hours. The suspension was then centrifuged and the pellet resuspended in 0.5 ml of 1.2 M sorbitol. Then, 6 ml of top agar (the SC medium of Sherman et al., (Methods in Yeast Genetics, Cold Spring Harbor Laboratory, 1981) containing 1.2 M sorbitol plus 2.5% agar) at 52° C. was added and the suspension poured on top of plates containing the same agar-solidified, sorbitol containing medium. Transformant colonies were picked after 3 days at 30° C., reisolated and used to start liquid cultures.

Transformant strains were grown on YPD medium (1% yeast extract, 2% peptone (from Difco laboratories), and 2% glucose) in a 1500 liter tank at 30° C. The expressed product was isolated from the culture broth.

Transpeptidation 0.2 mole (47.1 g) Thr-met, HOAC was dissolved in DMF to give 100 ml solution, 50 ml 76.5% v/v DMF in water was added and 10 g of crude B9Glu,B(1–29)-Ala-Ala-Lys-A12Glu,A(1–21) human insulin was dissolved in the mixture, which was thermostated at 12° C. Then 1 g of trypsin in 25 ml 0.05 M calcium acetate was added and after 24 hours at 12° C. the mixture was added to 2 liter of acetone and the precipitated peptides were isolated by centrifugation and dried in vacuo. The B9Glu,A21Glu,B30Thr-OMe human insulin was purified on a preparative HPLC column with silica-C18 as column material.

The B9Glu,A12Glu,B30Thr-OMe human insulin was dispersed in water to 1% (w/v) and was dissolved by addition of 1 N sodium hydroxide to a pH value of 10.0 . The pH value was kept constant at 10.0 for 24 hours at 25° C. The B9Glu,A12Glu human insulin formed was precipitated by addition of sodium chloride to about 8% (w/v), sodium acetate trihydrate to about 1.4% (w/v), and zinc acetate dihydrate to about 0.01% (w/v) followed by addition of 1 N hydrochloric acid to pH 5.5. The precipitate of B9Glu, A12Glu human insulin was isolated by centrifugation and purified by anion exchange chromatography and desalted by gel filtration.

I claim:

1. An insulin analogue having the general formula III:

B-Chain (contd.)

Phe–Xaa–Xaa–Xaa–Xaa–Xaa  (SEQ ID NO:6)
25   26   27   28   29   30 wherein the amino acid residue designated Xaa in at least one of the positions B9,B10,B16, B26,B28,B1,B2,B18,B20, B28, or A21 and furthermore an amino acid residue designated Xaa in at least one of the positions A5,A15,A18,B3, B4,A12,A14,B22,B29 or B30 is independently substituted by Asp or Glu while any remaining Xaa designated the amino acid residue occurring in human insulin in the pertinent position, the terminal ends of the B-chain optionally being extended by one or two amino acid residues which can be chosen independently among Asp and Glu, with the proviso that it no amino acid residue designated Xaa in position A12,A14,B22,B29 or B30 is substituted, or if the terminal ends of the B-chain have not been extended, then the total number of substitutions is at least five.

2. An insulin analogue according to claim 1 wherein two amino acid residues designated Xaa in positions B9,B10, B16,B28,B1,B2,B18,B20,B27 or A21 and furthermore an amino acid residue designated Xaa in at least one of the positions A5,A15,A18,B3,B4,A12,A14,B22,B29 or B30 independently is substituted by Asp or Glu while any remaining Xaa designates the amino acid residue occurring in human insulin in the pertinent position, the terminal ends of the B-chain optionally being extended by one or two amino acid residues which can be chosen independently among Asp and Glu.

3. An insulin analogue according to claim 1 wherein the total number of substitutions is at least five.

4. An insulin analogue according to claim 1 wherein one amino acid residue designated Xaa in position A12,A14, B22,B29 or B30 is substituted by Asp or Glu.

5. An insulin analogue according to claim 1 wherein two amino acid residues designated Xaa in position A12,A14, B22,B29 or B30 independently are substituted by Asp or Glu.

6. An insulin analogue according to claim 1 wherein three amino acid residues designated Xaa in position A12,A14, B22,B29 or B30 independently are substituted by Asp or Glu.

7. An insulin analogue according to claim 1 wherein one amino acid residue designated Xaa in position A5,A15,A18, B3, or B4 is substituted by Asp or Glu.

8. An insulin analogue according to claim 1 wherein two amino acid residues designated Xaa in position A5,A15, A18, B3, or B4 independently are substituted by Asp or Glu.

9. An insulin analogue according to claim 1 wherein three amino acid residues designated Xaa in position A5,A15, A18,B3, or B4 independently are substituted by Asp or Glu.

10. A pharmaceutical composition comprising an insulin analogue according to claim 1.

11. A method for administering the insulin analogue of claim 1 transdermally which comprises placing an aqueous medium of the insulin in contact with human skin then applying a direct current to said insulin medium and the skin in contact therewith so that at least 5 IU per day of the insulin analogue crosses the skin through iontophoresis.

* * * * *